United States Patent
Remmers et al.

(10) Patent No.: US 6,761,873 B1
(45) Date of Patent: Jul. 13, 2004

(54) METHOD FOR REDUCING THE BROMIDE CONTENT IN AN AQUEOUS BROMIDE-CONTAINING SOLUTION USING HYDROGEN PEROXIDE

(76) Inventors: Graalf Remmers, Rudolf-Wittrock-Strasse 6, D-30823 Garbsen (DE); Horst Lieker, Lister Kirchweg 55b, D-30165 Hannover (DE)

( * ) Notice: Subject to any disclaimer, the term of this patent is extended or adjusted under 35 U.S.C. 154(b) by 0 days.

(21) Appl. No.: 09/743,297

(22) PCT Filed: Jun. 30, 1999

(86) PCT No.: PCT/EP99/04515

§ 371 (c)(1),
(2), (4) Date: Feb. 20, 2001

(87) PCT Pub. No.: WO00/02815

PCT Pub. Date: Jan. 20, 2000

(30) Foreign Application Priority Data

Jul. 7, 1998 (DE) .......................................... 198 30 310

(51) Int. Cl.$^7$ .................................................. C01F 5/30
(52) U.S. Cl. ...................................... 423/497; 514/769
(58) Field of Search ............................ 423/497; 514/769

(56) References Cited

U.S. PATENT DOCUMENTS

| | | | | | |
|---|---|---|---|---|---|
| 3,729,550 | A | * | 4/1973 | Boyum et al. ............... | 423/497 |
| 4,756,838 | A | * | 7/1988 | Veltman ...................... | 210/646 |
| 5,112,584 | A | * | 5/1992 | Mejdell et al. ............. | 423/161 |
| 5,112,865 | A | * | 5/1992 | Nichels et al. ............. | 514/546 |
| 5,980,854 | A | * | 11/1999 | White et al. ................. | 423/158 |

* cited by examiner

*Primary Examiner*—Ngoc-Yen Nguyen

(57) ABSTRACT

The invention relates to a method for reducing the bromide content in an aqueous bromide-containing solution using hydrogen peroxide.

20 Claims, No Drawings

METHOD FOR REDUCING THE BROMIDE CONTENT IN AN AQUEOUS BROMIDE-CONTAINING SOLUTION USING HYDROGEN PEROXIDE

The present invention relates to a process for reducing the bromide content of a solution using hydrogen peroxide. The present invention also relates to a method in which, in addition to the bromide content, the bromate content is also reduced.

In many fields of application, for example chemistry or pharmacy, the maximum bromide content of chemical compounds used is a problem. Maintaining maximum limits of bromide concentration is of importance, inter alia, in the pharmaceutical industry.

When bromide-containing chemicals are used in the pharmaceutical sector, the purity requirements are based on the corresponding pharmacopoeias (Pharma Euro III, pp. 1234–1235). Compounds which are of importance in this connection are, for example, alkali metal compounds and alkaline earth metal compounds.

Especially in the case of alkali metal compounds and alkaline earth metal compounds of natural origin, the bromide content is an important problem, since numerous anions of, for example, alkali metal salts and alkaline earth metal salts are associated with bromide. For example, this applies to naturally occurring alkali metal chlorides and alkaline earth metal chlorides.

For magnesium chloride, the European Pharmacopoeia, for example, has required since Jan. 1, 1997, a limiting value for bromide content of 500 ppm.

A method for reducing the bromide content by which such a total bromine content of a compound may be achieved is, for example, the introduction of gaseous chlorine into a solution of the corresponding compound in a suitable solvent, for example water.

DE-A 21 18 623 discloses, for example, a method for purifying aqueous magnesium chloride solutions in which the bromide content is reduced by introducing chlorine gas into these solutions.

DE-A 26 13 28 describes a method for preparing highly concentrated magnesium chloride solutions. The debromination described in this publication takes place hot using gaseous chlorine.

However, handling gaseous chlorine, owing to the reactivity of this gas, represents a high hazard potential. Therefore, the corresponding methods and experimental setups, for safety reasons, generally have high equipment requirements and thus also high financial outlay.

An object of the present inventions was therefore to provide an industrial method which is simple to carry out in terms of apparatus and in which bromide can be reduced in solutions.

This object has been achieved by using hydrogen peroxide as oxidizing agent for bromide. Accordingly, the present invention relates to a method for reducing the bromide content of a solution using hydrogen peroxide.

The most important compounds whose solutions are treated by the inventive method to reduce the bromide content include alkali metal compounds and alkaline earth metal compounds.

The present invention therefore also relates to a method which is characterized in that the aqueous solution is a solution of alkali metal compounds and/or alkaline earth metal compounds.

In particular, the present invention relates to a method which is characterized in that the alkali metal compounds and alkaline earth metal compounds are alkali metal chlorides and alkaline earth metal chlorides.

Generally, in the inventive method, it is not critical at what concentration hydrogen peroxide is used. In particular, it is possible to adapt this concentration to the requirements of the purification. Those which may be mentioned are, for example, the contamination of the solution, that is to say its bromide content or its content of other impurities which can be oxidized by hydrogen peroxide.

The pH of the solution whose bromide content is to be reduced is generally in the inventive method in the range <7, preferably in the range $\leq 6$, and particularly preferably in the range $\leq 5$.

The present invention therefore relates to a method as described above which is characterized in that the aqueous solution has a pH of $\leq 5$ during the reduction.

The pH of the solution is set in the inventive method to the desired value via acids or bases, depending on the initial pH of the solution.

Generally, the addition of acids is necessary in order to bring the pH to the desired values as described above. Acids which are preferably used are inorganic acids. Particular preference is given here to hydrochloric acid.

Obviously, it is possible within the context of the inventive method to add the acid, if necessary, in the gaseous state to the solution. However, preference is given to addition of the acid in solution.

The required amount of acid can bet adapted here to operational requirements of the experiment. It is only necessary to ensure that, after adding the acid and hydrogen peroxide, the pH of the solution is in the desired range, as described above.

Preferably, the content of free acid of the solution to be depleted is in the range from 0.01 to 25% by weight, particularly preferably in the range from 0.1 to 10% by weight, and in particular in the range from 0.3 to 5% by weight.

The sequence of addition of acid and hydrogen peroxide is generally not critical here. It is conceivable, for example, that firstly acid is added to the solution to be depleted and subsequently thereto hydrogen peroxide.

The reverse sequence is also possible. The bromine formed by oxidation in th e course of the method can, in the inventive method, be removed from the solution by all methods known from the prior art.

In particular, the removal process can be performed by boiling or stripping the solution. It is also conceivable to apply a vacuum to the solution.

Obviously, it is also conceivable to combine suitable methods. Thus, it is possible, for example, to heat the solution and at the same time to apply a vacuum. Therefore, the present invention also relates to a method as described above which is characterized in that the bromine formed during the depletion is removed from the solution by boiling the solution, stripping the solution and/or by applying a vacuum to the solution.

If bromine is removed from the solution solely by stripping, air is injected into the solution at a throughput of generally from 1 to 100, preferably from 2 to 50, particularly preferably from 3 to 20, 1/min.

Regardless of the method which is used in the removal process, in the inventive method, after the depletion, bromide contents are found which are <500 ppm, preferably <300 ppm, particularly preferably <100 ppm, further particularly preferably <50 ppm, in particular <25 ppm.

The present invention therefore also relates to a method as described above which is characterized in that the bromide content of the depleted solution is less than 25 ppm.

A further advantage of the inventive method is based on the fact that simultaneously with bromide bromate, where present, can also be removed from the solution. The present invention therefore also relates to a method as described above which is characterized in that, in addition to the bromide content, the bromate content of the solution is reduced.

Hydrogen peroxide is particularly useful here when the bromate content of the solution is higher than its bromide content.

In its most general form the invention relates to the use of hydrogen peroxide for reducing the bromide content of a bromide-containing aqueous solution.

The present invention further relates to the use of hydrogen peroxide for reducing the bromate content of bromide- and bromate-containing aqueous solutions.

The present invention also relates to the use of hydrogen peroxide for removing bromide or bromate or a mixture of bromide and bromate from an aqueous solution that is used in the production of medicaments.

The present invention also relates to the use of high-purity magnesium chloride for hemodialysis, hemofiltration or peritoneal dialysis solutions and parenteral applications, in particular infusion solutions, which can be prepared by crystallization of a magnesium chloride solution, characterized in that, prior to the crystallization, the bromide content of the magnesium chloride solution was reduced using hydrogen peroxide.

The present invention is to be described below by an exemplary embodiment.

EXAMPLE

An aqueous solution contained 67% by weight of $MgCl_2 \cdot 6H_2O$, 0.093% by weight of bromide and 2% by weight of free HCl.

1000 g of this original solution were transferred in each case into two 2000 $cm^3$ glass beakers and to one 2000 $cm^3$ flask.

The beakers were used to remove, after later addition of hydrogen peroxide, the resultant bromine by boiling or stripping and by withdrawing it via suction feeding it to suitable absorption.

The flask was used, after addition of hydrogen peroxide, to remove the resultant bromine by applying vacuum.

After adding 5 g each time of 35% strength by weight aqueous hydrogen peroxide solution to each individual solution, the experiments were started. The solutions in the two glass beakers were heated to boiling or stripped by injecting air at 4 l/min. The total volume of the solution was kept constant by adding ultrapure water.

The third experiment was carried out by applying vacuum (30 torr) to the flask.

Regardless of the removal method selected, in all three experiments, bromide contents of <25 ppm were found by ion-chromatographic analysis.

What is claimed is:

1. A process for providing magnesium chloride containing less than 500 ppm of bromide ion, comprising: i) providing a magnesium chloride solution prepared from magnesium chloride containing more than 500 ppm of bromide ions and which solution optionally also contains bromate ions; and ii) contacting said solution with hydrogen peroxide.

2. The process of claim 1, wherein said magnesium chloride solution is an aqueous solution.

3. The process of claim 1, further comprising the step of adjusting said solution to a pH of ≦5 before or after contact with hydrogen peroxide.

4. The process of claim 2, further comprising the step of adjusting said solution to a pH of less than or equal to about 5, wherein the adjustment can be made before or after contact with hydrogen peroxide.

5. The process of claim 1, wherein said magnesium chloride has a bromide ion content of less than 25 ppm.

6. The process of claim 2, wherein said magnesium chloride has a bromide ion content of less than 25 ppm.

7. The process of claim 3, wherein said magnesium chloride has a bromide ion content of less than 25 ppm.

8. The process of claim 4, wherein said magnesium chloride has a bromide ion content of less than 25 ppm.

9. The process of claim 1 wherein the magnesium chloride solution provided in step "i" contains also bromate ion.

10. The process of claim 2, wherein the magnesium chloride solution provided in step "i" contains also bromate ion.

11. The process of claim 3, wherein the magnesium chloride solution provided in step "i" contains also bromate ion.

12. The process of claim 1, further comprising a magnesium chloride crystallization step following said step ii) step.

13. The process of claim 8, further comprising a magnesium chloride crystallization step following said step ii) step.

14. The process of claim 3, further comprising a magnesium chloride crystallization step following said steps ii) an said pH adjustment step.

15. The process of claim 4, further comprising a magnesium chloride crystallization step following said step ii) an said pH adjustment step.

16. A process for reducing the bromate ion concentration in an aliquot of magnesium chloride comprising:

i) providing a bromate ion-containing magnesium chloride solution; and ii) contacting hydrogen peroxide with said magnesium chloride solution.

17. The method of claim 16 further comprising the step of adjusting the solution pH to a value equal to or less than about pH 5, wherein the pH adjustment can be provided before or after the hydrogen peroxide contacting step.

18. The process of claim 17, further comprising a crystallization step following both of said peroxide contacting and said optional pH adjusting steps.

19. In a process for preparing a pharmaceutical formulation which requires the provision of magnesium chloride containing less than 500 ppm of bromide ion, the improvement comprising: (i) lowering the concentration of bromide ion and if present bromate ion in an aliquot of magnesium chloride containing more than 500 ppm of bromide by the process of claim 12, (ii) isolating crystallized magnesium chloride from said process; and (iii) providing said isolated magnesium chloride to said process for preparing a pharmaceutical formulation.

20. The process of claim 19 wherein said pharmaceutical formulation is a dialysis solution.

* * * * *